(12) United States Patent
Arata et al.

(10) Patent No.: US 7,261,905 B2
(45) Date of Patent: *Aug. 28, 2007

(54) DISINFECTANT AND METHOD OF MAKING

(75) Inventors: Andrew B. Arata, Lake City, FL (US); Michael L. Krall, El Cajon, CA (US)

(73) Assignee: Pure Bioscience, El Cajon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/434,742

(22) Filed: May 9, 2003

(65) Prior Publication Data

US 2003/0198689 A1 Oct. 23, 2003

Related U.S. Application Data

(63) Continuation of application No. 09/544,404, filed on Apr. 6, 2000, now abandoned.

(60) Provisional application No. 60/128,212, filed on Apr. 7, 1999.

(51) Int. Cl.
- A01N 55/02 (2006.01)
- A01N 59/16 (2006.01)
- A01N 59/00 (2006.01)
- A01N 37/04 (2006.01)
- C25B 3/00 (2006.01)
- C25B 3/12 (2006.01)

(52) U.S. Cl. ............... 424/618; 424/DIG. 6; 514/495; 514/574; 514/836; 514/970; 205/440; 205/457

(58) Field of Classification Search ............... 514/495, 514/553–574, 576, 578, 184, 836, 970; 424/618, 424/619, DIG. 6; 422/22, 28; 205/440, 205/457

See application file for complete search history.

(56) References Cited

U.S. PATENT DOCUMENTS

| | | | |
|---|---|---|---|
| 3,422,183 A | 1/1969 | Ellison | |
| 3,702,298 A | 11/1972 | Zsoldos | |
| 4,021,578 A | 5/1977 | Harich et al. | |
| 4,180,473 A | 12/1979 | Maurer et al. | |
| 4,264,592 A | 4/1981 | Xhajanka | |
| 4,291,125 A | 9/1981 | Greatbatch | |
| 4,297,374 A | 10/1981 | Wess | |
| 4,385,632 A | 5/1983 | Odelhog | |
| 4,564,461 A | 1/1986 | Skold et al. | |
| 4,608,183 A | 8/1986 | Rossmoore | |
| 4,666,616 A | 5/1987 | Rossmoore | |
| 4,708,808 A | 11/1987 | Rossmoore | |
| 4,755,268 A | 7/1988 | Matsuo et al. | |
| 4,780,216 A | 10/1988 | Wojtowicz | |
| 4,889,844 A | 12/1989 | Silvetti, Sr. et al. | |
| 4,915,955 A | 4/1990 | Gomori | |
| 4,933,178 A | 6/1990 | Capelli | |
| 5,017,295 A | 5/1991 | Antelman | |
| 5,063,062 A | 11/1991 | Greenspan et al. | |
| 5,073,382 A | 12/1991 | Antelman | |
| 5,078,902 A | 1/1992 | Antelman | |
| 5,089,275 A | 2/1992 | Antelman | |
| 5,177,065 A | 1/1993 | Silvetti, Sr. et al. | |
| 5,332,511 A | 7/1994 | Gay et al. | |
| 5,362,714 A | 11/1994 | Radford et al. | |
| 5,364,649 A | 11/1994 | Rossmoore et al. | |
| 5,373,025 A | 12/1994 | Gay | |
| 5,382,337 A | 1/1995 | Wlassics et al. | |
| 5,464,559 A | 11/1995 | Marchin et al. | |
| 5,503,840 A | 4/1996 | Jacobson et al. | |
| 5,510,109 A | 4/1996 | Tomioka et al. | |
| 5,660,840 A | 8/1997 | Pruett | |
| 5,962,517 A | 10/1999 | Murad | |
| 6,017,461 A | 1/2000 | Garvey et al. | |
| 6,139,823 A | 10/2000 | Drechsler et al. | |
| 6,181,963 B1 | 1/2001 | Chin et al. | |
| 6,197,814 B1 | 3/2001 | Arata | |
| 6,478,946 B1 * | 11/2002 | Westwood | 205/571 |
| 6,583,176 B2 | 6/2003 | Arata | |
| 6,838,095 B2 * | 1/2005 | Newman et al. | 424/618 |

FOREIGN PATENT DOCUMENTS

WO    WO96/28390    9/1996

OTHER PUBLICATIONS

Chemical Abstracts 118:156836t (1993).*
U.S. Appl. No. 60/107,710, filed on Nov. 9, 1998.*
U.S. Appl. No. 09/119,741, filed on Jul. 21, 1998.*
DERWENT Abstract, accession No. 2000-268443, abstracting RU 2125971 (Feb. 10, 1999).*
Chemical Abstracts. 87:74283n Complexes of Silver (I) with Some Hydroxy Acids. Tsimbler, S. M.; Novikova, L.S. (USSR). Zh Neorg. Khim. 1977, 22 (7) 1842-6 (Russ).
Chemical Abstracts. 69.8964n Preservatives for Tobacco Paul Richli. Swiss 446691 (Cl. A 24b) Mar. 15, 1968, Appl. Apr. 22, 1964; 2pp.

* cited by examiner

*Primary Examiner*—John Pak
(74) *Attorney, Agent, or Firm*—Needle & Rosenberg, P.C.

(57) ABSTRACT

A non-toxic environmentally friendly aqueous disinfectant is disclosed for specific use as prevention against contamination by potentially pathogenic bacteria and virus. The aqueous disinfectant is formulated by electrolytically generating silver ions in water in combination with a citric acid. The aqueous disinfectant may include a suitable alcohol and/or a detergent. The aqueous disinfectant has been shown to be very effective at eliminating standard indicator organisms such as *staphylococcus aureus, salmonella cholerasuis* and *pseudomonas aeruginosa*.

13 Claims, 3 Drawing Sheets

DISINFECTANT AND METHOD OF MAKING

CROSS-REFERENCE TO RELATED APPLICATIONS

This is a continuation of U.S. patent application Ser. No. 09/544,404 filed Apr. 6, 2000, now abandoned. U.S. patent application Ser. No. 09/544,404 filed Apr. 6, 2000, now abandoned claims benefit of U.S. Patent Provisional application Ser. No. 60/128,212 filed Apr. 7, 1999. All subject matter set forth in U.S. patent application Ser. No. 09/544,404, filed Apr. 6, 2000, now abandoned and U.S. provisional application Ser. No. 60/128,212, filed Apr. 7, 1999, is hereby incorporated by reference into the present application as if fully set forth herein.

BACKGROUND OF THE INVENTION

1. Field of the Invention

This invention relates to disinfectants and more particularly to an environmentally friendly, non-toxic aqueous disinfectant for specific use against pathogenic bacteria and viruses.

2. Prior Art Statement

The prior art has demonstrated that the presence of copper and silver ions in an aqueous solution is useful as a disinfectant. Many in the prior art have used copper and silver ions in an aqueous solution as a disinfectant in water systems such as cooling towers, swimming pools, hot water systems in hospitals, potable water systems, spa pools and the like.

Typically, copper and silver electrodes were connected to a direct current power supply. When the direct current was applied to the copper and silver electrodes, copper and silver ions were generated by an electrolysis process producing copper and silver ions within the water. In one example of the prior art, water was passed continuously through an ion chamber having copper and silver electrodes. The water emanating from the ion chamber contained the copper and silver ions generated by copper and silver electrodes within the ion chamber. The water emanating from the ion chamber containing the copper and silver ions was used as a disinfectant in water systems such as cooling towers, swimming pools, hot water systems in hospitals, potable water systems, spa pools and the like. The copper and silver ions within the water systems acted as a disinfectant for controlling algae, viruses, bacteria and the like.

U.S. Pat. No. 3,422,183 to Ellison discloses biocide compositions comprising ultra-violet irradiated silver fluoride solutions containing colloidal silver resulting from the irradiation and kept in dispersion by a protective colloid, e.g., casein or gelatin, and biocide uses thereof in slime control, against pathogens or other microbes in food or beverage containers or processing equipment, as an ingredient of wood preservatives, as a bactericide in paints, as a biocide in synthetic polymer films, as a sterilant in bandages, and biocide-like uses in other areas.

U.S. Pat. No. 3,702,298 to Zsoldos discloses a method of maintaining a highly oxidizing aqueous solution intended primarily for treatment of swimming pool water. A metal having a multiple valence is interacted to a lower valence with oxidizable debris in the solution, and the metal is continuously re-oxidized to a higher valence by maintaining in the water a constant excess of an oxidizer bank consisting of a salt of a peroxy acid. Silver, copper and nickel are suitable metals and their salts have germicidal properties which are greatly increased and the spectrum broadened by converting the mono salt to a divalent or trivalent salt.

U.S. Pat. No. 4,180,473 to Maurer et al. discloses a method of transporting metal ions by introducing a metal complex into a medium containing a moiety which demands the metal ion and the complex releases the ions in a controlled manner upon demand. The metal complexes have an aqueous proton induced dissociation property represented by a sigmoidally-shaped curve on a Cartesian coordinate plot of the negative log of the metal ion concentration versus the negative log of hydrogen ion concentration. This dissociation property causes a controlled release of metal ion into mediums containing a reacting moiety upon demand for the metal ion. For example, metal working emulsions of oil and water are stabilized by the addition thereto of minor amounts of a metal complex, e.g. disodium monocopper (II) citrate, which at alkaline pH metalworking conditions above about 7 to about 9 releases metal cations to the emulsions imparting stabilizing characteristics which prevent emulsion degradation by a number of factors commonly encountered in metalworking operations. Also, the method is effective in the controlled release of metal ions in the normal range of physiological pH, i.e. about 4 to 9, for growth controlling action against microorganisms including bacteria, fungi and viruses.

U.S. Pat. No. 4,291,125 to Greatbatch discloses a method and apparatus for killing plant and animal bacteria and plant viroids by electrically generated silver ions. The silver ions serve as germicidal agents in infection control and are generated by very slow electrical anodic corrosion of a silver wire located closely adjacent the infection site. In particular, a silver anode and a cathode of non-corroding metal are located in an electrolytic nutrient medium with the silver anode being within five millimeters of the infection site, and a direct voltage is applied to the anode and cathode in a manner passing a positive current in the microampere range into the silver anode causing it to corrode slightly and give off silver ions which produce a germicidal environment about the infection site.

U.S. Pat. No. 4,385,632 to Odelhog discloses an absorbent body for collecting blood, feces and urine containing a water-soluble copper salt which impedes bacterial growth, prevents the breaking-down of urea into ammonia and complex-binds ammonia so as to prevent the occurrence of unpleasant odor. Preferably copper acetate is used, in which even the acetate ion has germicidal effect.

U.S. Pat. No. 4,564,461 to Skold et al. discloses mechanical working of cast iron performed in the presence of an aqueous metal working composition containing an organic copper (II) complex and an iron corrosion inhibitor. An aqueous concentrate, which after dilution with water is suitable for application in mechanical working of cast iron, contains 1-50% copper (II) complex with such a $Cu_2+$ content of 0.5-20%, 1-50% iron corrosion inhibitor, 0-50% lubricant, 0-20% pH-regulators, bactericides and solubilizing agents and 10-70% water.

U.S. Pat. No. 4,608,183 to Rossmoore discloses antimicrobial mixtures of isothiazolones and a metal complex with a polyfunctional ligand which are synergistic. The mixtures particularly include mixtures of a monocopper disodium citrate as the ligand and a 5-x-2-lower alkyl 4-isothiazolin-3-one wherein x is a halo or hydrogen group as the isothiazolone. The compositions are particularly useful for metal cutting fluids wherein long duration antimicrobial activity is desired.

U.S. Pat. No. 4,666,616 to Rossmoore discloses synergistic anti-microbial compositions containing a mixture of a metal complex of a polyfunctional organic liquid and a biocidal composition which contains or releases a lower aldehyde containing 1 to 5 carbon atoms. The compositions are particularly useful as metal working fluids at alkaline pH and have a broad spectrum of activity against fungi and bacterial.

U.S. Pat. No. 4,708,808 to Rossmoore discloses synergistic anti-mircrobial compositions containing a mixture of a metal complex of a polyfunctional organic ligand and a biocidal composition which contains or releases a lower aldehyde containing 1 to 5 carbon atoms. The compositions are particularly useful as metal working fluids at alkaline pH and have a broad spectrum of activity against fungi and bacteria.

U.S. Pat. No. 4,780,216 to Wojtowicz discloses a sanitizing composition consisting essentially of a mixture of a calcium hypochlorite compound and a peroxydisulfate compound having the formula: $M_xS_2O_8$ where M is an alkali metal or alkaline earth metal, and x is 1 or 2 is employed in treating water to improve pH control and provide increased removal of organic materials. The compositions provide improved sanitation of water in swimming pools, spas, and cooling towers by efficiently oxidizing organic impurities while helping to minimize the increase in the pH of the water. This permits a reduction in the amount and frequency of addition of acidic compounds such as hydrochloric acid to the water bodies. Further, the incorporation of additives such as algaecides, dispersant, and clarifying agents provides for significant improvements in water quality as evidenced by sparkling pure water.

U.S. Pat. No. 4,915,955 to Gomori discloses a concentrate with an unlimited shelf-life, which can be mixed with hydrogen peroxide at a ratio of 1:99 to 1:199 to become an effective disinfectant, is obtained when a viscous solution of inorganic acid, with a pH less than or equal to 1.6, is mixed with a silver salt compound or a colloidal silver compound at 50° to 66° C. The mixture is further combined at room temperature with other inorganic acid(s) to reach a total of 100 g inorganic acid(s) per liter of water at room temperature, an organic acid stabilizer is added and the mixture is homogenized. The concentrate, during storage, remains homogeneous and crystal-clear.

U.S. Pat. No. 4,933,178 to Capelli discloses a medical device with an antimicrobial coating that is safe, effective, photostable and readily manufacturable produced by applying a composition to at least one body fluid-contacting surface of the device such that a solid coating is provided on that surface, the coating composition comprising an oligodynamic metal salt of a sulfonylurea, a polymeric material, at least one acid compound selected from the group consisting of a water-soluble carboxylic acid and water-insoluble carboxylic acid, and a carrier liquid in which foregoing components are soluble. The antimicrobial coating accommodates variation in the release of antimicrobial metal ions as a function of the intended use for a medical device to which the coating is applied.

U.S. Pat. No. 5,017,295 to Antelman discloses a method or methods of controlling the growth of bacteria in the water of swimming pools and/or industrial water supplies by adding to the water a specified concentration of a stable divalent silver compound. The invention has the advantage over chlorination in that it is odorless and non-volatile. It furthermore is superior to monovalent silver compounds as these compounds do not decompose in the presence of light and resist precipitation by halides and form divalent soluble complexes which in the monovalent state are invariably insoluble solids.

U.S. Pat. No. 5,073,382 to Antelman discloses a solid alkaline bactericidal composition suitable for compounding alkaline end products such as food and dairy cleaners and surgical scrubbing soaps, formed by the neutralization of acid stabilized inorganic divalent silver complexes and capable of effecting 100% kills upon cultures of anaerobic bacteria colonies of 100 K/cc. within 5 minutes.

U.S. Pat. No. 5,078,902 to Antelman discloses divalent silver halides providing a source for divalent bactericidal silver ions in the presence of persulfate. The halides are especially effective when applied to water used in industrial cooling installations, hot tubs and swimming pools and will conform to stringent EPA requirements for waters utilized for bathing as in tubs and pools of 100% kills of 100 K/cc *E. Coli* coliforms within 10 minutes, exemplary of which are the chloride and bromide which give 100% kills within 5 minutes. The halides, of course, can be used in salty water since they are solids immune from halide action that would otherwise precipitate soluble divalent silver from solution.

U.S. Pat. No. 5,089,275 discloses solid bactericidal compositions based on divalent silver (Ag(II)) as the active sanitized agent. The compositions are prepared by reacting acid liquid Ag(II) complexes with anhydrous calcium sulfate so as to form a solid matrix in which the bactericide is entrapped in the resulting hydrated calcium sulfate. The optimum compositions are described consisting of Ag(II) of solid (by weight) to liquid (by volume) being 5:2. The resulting solid bactericides can be used in water cooling installations. They are capable of causing 100% kills within 10 minutes of *E. Coli* conforms in conformity with EPA protocols, allowing them to qualify as swimming pool and hot tub sanitizers. Since the compositions are based on calcium sulfate, they are also suitable as mineralizers, thus providing a dual function.

U.S. Pat. No. 5,332,511 to Gay et al. discloses a process for sanitizing water in swimming pools, spas and hot tubs whereby the level of bacteria in said water is lowered comprising treating said water with a bactericidal effective amount of a combination of diisodecyl dimethyl ammonium chloride and copper (II) ions, the concentration of diisodecyl dimethyl ammonium chloride in said water being less than about 60 parts per million parts of water by weight and treating said water at least intermittently with an oxidant selected from the group consisting of available chlorine and ozone.

U.S. Pat. No. 5,364,649 to Rossmoore et al. discloses activity of antimicrobial compounds selected from isothiazolones and compounds which release formaldehyde enhanced with a metal complex of a lower alkanolamine, particularly copper (cupric) trietha-iolamine. The enhancement is particularly useful in metalworking fluids.

U.S. Pat. No. 5,373,025 to Gay discloses a sanitizer composition comprising a bactericidal effective amount of the combination of (a) a quaternary ammonium compound selected from the group consisting of (hydrogenated tallow) 2-ethylhexyl dirnethyl ammonium salt, dicoco dimethyl ammonium salt, and mixtures thereof; and (b) a copper (II) ion source.

U.S. Pat. No. 5,382,337 to Wlassics et al. discloses a process for oxidizing organic materials or compounds in aqueous phase, with hydrogen peroxide and in the presence of ferrous ions Fe(II), and optionally cupric ions Cu-(II), carried out under irradiation with artificial visible light.

U.S. Pat. No. 5,464,559 to Marchin et al. discloses a composition provided for treating drinking water for disinfecting and/or removing iodide. The composition utilizes resin bound silver ions. For performing the disinfection or iodide removal with minimal release of silver ions into the water being treated, a chelating resin having iminodiacetate chelating groups is employed, and the resin is loaded with not over 0.5 mole of silver ions per mole of iminodiacetate.

U.S. Pat. No. 5,503,840 to Jacobson et al. discloses an antimicrobial composition of titanium dioxide, barium sulfate, zinc oxide particles, and mixtures thereof having successive coatings of silver, in some cases a coating of zinc and/or copper compounds such as zinc oxide, copper (II) oxide and zinc silicate; silicon dioxide; alumina; and a dispersion aid such as dioctyl azelate.

U.S. Pat. No. 5,510,109 to Tomioka et al discloses an antibacterial and antifungal composition which comprises an antibacterial and antifungal material carried on a porous particle carrier. Preferably, the porous particle carrier is a silica gel particle. The antibacterial and antifungal material is at least one metal complex salt, and can contain plant extracts and the like in addition to the metal complex salt. At least a portion of the surface of the above-mentioned carrier having the antibacterial and antifungal composition can be coated with a coating material.

Unfortunately, these copper and silver ions within an aqueous solution have only a limited stable ionic life. After a limited time, the copper and silver ions form complexes with other elements thus diminishing the concentration of the copper and silver ions within the aqueous solution. Accordingly, the aqueous solution had to be replenished with copper and silver ions to maintain the concentration of the copper and silver ions within the aqueous solution. The aqueous solution may be replenished with copper and silver ions by constantly circulating the aqueous solution thorough the ion chamber.

In my prior U.S. patent application Ser. No. 09/169,229 filed Oct. 9, 1998, now U.S. Pat. No. 6,197,814, and Internation application PCT\US98\21604, I disclosed an aqueous disinfectant solution having a stable ionic form having an extended useful shelf-life. The extended useful shelf-life of the disinfectant of the present invention enables the disinfectant to be packaged in an aqueous concentrate form. The extended useful shelf-life of the aqueous disinfectant solution enables the aqueous disinfectant solution to be packaged in an aqueous concentrate form.

It is an object of the present invention to expand upon my prior invention by providing an improved disinfectant and the method of making comprising an aqueous disinfectant for specific use as prevention against contamination by potentially pathogenic bacteria and virus and antifungal properties.

Another object of this invention is to provide an improved disinfectant and the method of making which is an effective disinfectant for eliminating standard indicator organisms such as *staphylococcus aureus, salmonella cholerasuis* and *pseudomonas aeruginosa.*

Another object of this invention is to provide an improved disinfectant and the method of making which is a non-toxic, environmentally friendly aqueous disinfectant.

Another object of this invention is to provide an improved disinfectant and the method of making which comprises a stable ionic formulation having an extended useful shelf-life.

Another object of this invention is to provide an improved disinfectant and the method of making which may be packaged in a concentrated aqueous form.

Another object of this invention is to provide an improved disinfectant and the method of making which may be electrolytically generated in a batch process or a continuous process.

Another object of this invention is to provide an improved disinfectant and the method of making which is electrolytically generated in an economical manner.

Another object of this invention is to provide an improved disinfectant and the method of making which is suitable for use with an alcohol and/or a detergent.

Another object of this invention is to provide an improved disinfectant and the method of making which may be used on exposed and/or contaminated surfaces to kill bacteria, virus, fungi and other micro-organisms.

Another object of this invention is to provide an improved disinfectant and the method of making which may be used on contaminated open wounds and tissue, dermal wound sites and/or lesions of living organisms such as animals and humans.

Another object of this invention is to provide an improved disinfectant and the method of making which may be used on exposed surfaces in food processing plants, residential, hospital, restaurants, public facilities and the like.

Another object of this invention is to provide an improved disinfectant and the method of making which may be used to control bio-film, microbes, algae and the like.

Another object of this invention is to provide an improved disinfectant and the method of making which may be used to control microbes in or on agricultural and food items and drinking water.

Another object of this invention is to provide an improved disinfectant and the method of making which may be used to control microbes in paint additive for mildew control in paints.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention with in the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

A specific embodiment of the present invention is described and shown in the attached Detailed Description. For the purpose of summarizing the invention, the invention relates to an improved non-toxic environmentally friendly aqueous disinfectant for use as a prevention against contamination by potentially pathogenic bacteria, virus and fungi. The improved aqueous disinfectant is suitable for use on exposed surfaces. In addition, the improved aqueous disinfectant is suitable for use on dermal wound sites and lesions of living organisms such as animals and humans. The aqueous disinfectant pH varies from 2 to 7.

The aqueous disinfectant is incorporated into an aqueous solution of silver ion organic acid complex wherein the silver is electrolytically generated in a solution of the organic acid and water. The electrolytically generated silver forms an organic metal complex with the organic acid. In one example of the invention, the electrolytically generated silver forms a complex with the organic acid of $(Ag(CO)x)+(OA)-$, wherein OA is an organic acid selected from a group of organic acids having the characteristic of an acid as well as the characteristic of an alcohol. In another example of the invention, the electrolytically generated silver forms a complex with the organic acid of (Ag(CO)x)+(OA)−, wherein OA is an organic acid selected from a group consisting of ascorbic acid, citric acid, glycollic acid, lactic acid, maleic acid, tartaric acid. In a further example of the invention, the electrolytically generated silver forms a complex with the organic acid of (Ag(CO)x)+(OA)−, wherein OA is an organic acid selected from a group consisting of acetic acid, aspartic acid, cis-cyclohexane dicarboxylic acid, chloracetic acid, dl-cysteine acid, dl-cyctine acid, malic, malonic acid, propionic acid, succinic acid.

The aqueous disinfectant may be combined with an alcohol such as ethyl alcohol (EtOH) and/or a detergent such as sodium dodecyl sulfate.

The invention is also incorporated into the process of making the disinfectant comprising the step of electrolytically generating silver in a solution of organic acid and water to form an aqueous solution of the silver organic acid. The process may include creating a solution of approximately 2% or greater organic acid in water by volume. A positive silver electrode is spaced relative to a negative electrode for enabling the solution to be located therebetween. A potential difference is applied to the positive and negative electrodes to establish a flow of silver ions between the positive and negative electrodes for enabling the silver ions to react with the organic acid to form silver ion-organic acid complex thereby.

The invention is also incorporated into the process of making silver ion organic acid complex, comprising the step of electrolytically generating silver in a solution of an organic acid and water to formed an aqueous solution of the silver ion organic acid complex. A process of making the silver ion organic acid complex comprises the step of electrolytically generating silver in a solution of greater than 1% organic acid and water to form an aqueous solution of a silver ion-organic acid complex wherein the organic acid has the characteristic of an acid as well as the characteristic of an alcohol. Another embodiment of a process of making the silver ion organic complex comprises the step of electrolytically generating silver in a solution of greater than 1% organic acid and water to form an aqueous solution of a silver ion-organic acid complex wherein the organic acid is selected from the group consisting of ascorbic acid, citric acid, glycolic acid, lactic acid, malic acid and tartaric acid. Another embodiment of a process of making the silver ion organic complex comprises the step of electrolytically generating silver in a solution of greater than 1% organic acid and water to form an aqueous solution of a silver ion-organic acid complex wherein the organic acid is selected from the group consisting of acetic acid, aspartic acid, cis-cyclohexane dicarboxylic acid, chloroacetic acid, dl-cysteine, dl-cystine, malic acid, malonic acid, propionic acid, and succinic acid.

The foregoing has outlined rather broadly the more pertinent and important features of the present invention in order that the detailed description that follows may be better understood so that the present contribution to the art can be more fully appreciated. Additional features of the invention will be described hereinafter which form the subject of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several Figures of the drawings.

DETAILED DISCUSSION

Process of Making

Figure 1:
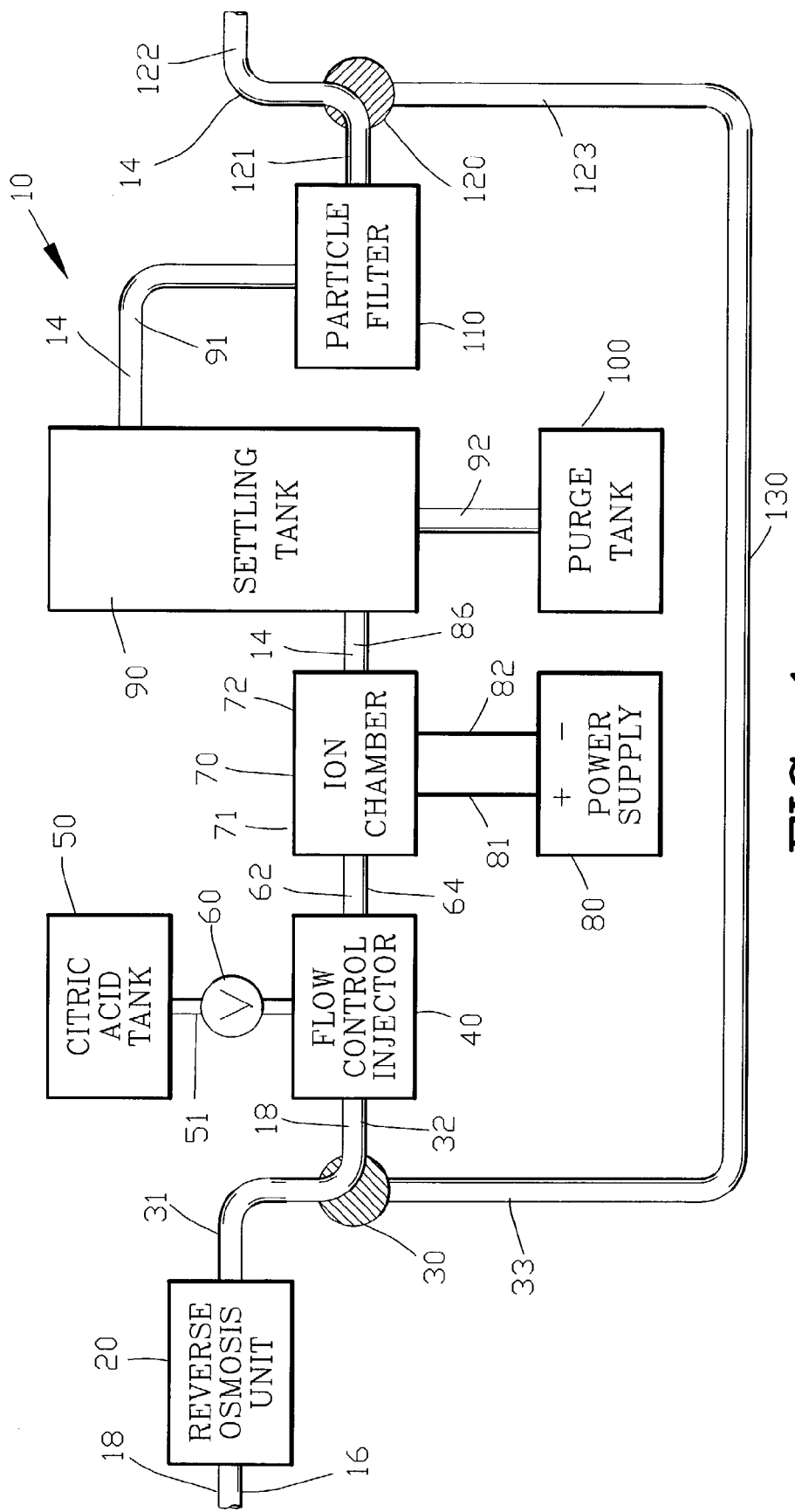
FIG. 1 is a diagram of a first process of making the disinfectant of the present invention.

FIG. 1 is a diagram of a first process 10 of making the disinfectant 14 of the present invention. The first process 10 is shown as a continuous process of making the disinfectant 14. It should be understood that the first process 10 of FIG. 1 is only an example of a process and numerous other variations and/or processes may be utilized to make the disinfectant 14 of the present invention.

The disinfectant 14 may be used immediately for any suitable application such as a disinfectant in a water system including cooling towers, hot water systems, potable water systems, or any other suitable application or surface.

The first process 10 comprises a water input conduit 16 for introducing water 18 from a water source (not shown) to a water treatment unit shown as a reverse osmosis unit 20. The reverse osmosis unit 20 passes the water 18 from the water input conduit 16 through a semi-permeable membrane (not shown) for removing impurities from the water. Although the water treatment unit is shown as a reverse osmosis unit 20 it should be understood that various water treatment units may be employed within the process shown in FIG. 1. Preferably, the water 18 emanating from the reverse osmosis unit 20 is deionized medically pure water.

The water 18 emanating from the reverse osmosis unit 20 is directed to a valve 30 through a conduit 31. The valve 30 directs the water 18 though a conduit 32 to a flow control injector 40. An organic acid tank 50 contains concentrated organic acid. The concentrated organic acid is directed by a conduit 51 to a metering valve 60 for metering the concentrated organic acid into the flow control injector 40. The flow control injector 40 mixes the concentrated organic acid with the water 18 to provide a dilute organic acid solution 62. The metering valve 60 controls the concentration of the organic acid within the water 18. The diluted organic acid solution 62 is directed by a conduit 62 into an ion chamber 70.

Figure 3:
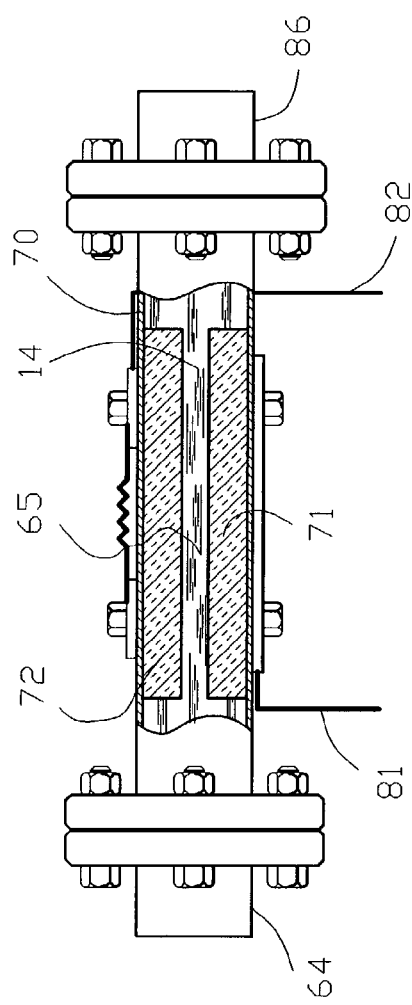
FIG. 3 is an enlarged detailed view of the ion chamber of FIGS. 1 and 2.

FIG. 3 is an enlarged detailed view of the ion chamber 70 of FIG. 1. The ion chamber 70 includes a positive and a negative electrode 71 and 72. The positive and negative electrodes 71 and 72 are located in a spaced apart position for enabling the diluted organic acid solution 62 to pass between the positive and negative electrodes 71 and 72. Each of the positive and negative electrodes 71 and 72 is fabricated from elemental silver. Preferably, the positive and negative electrodes 71 and 72 are formed from 99.9999% pure elemental silver.

A direct current power supply 80 includes a positive and a negative conductor 81 and 82 connected to the positive and negative electrodes 71 and 72. The positive and negative electrodes 71 and 72 are spaced apart a suitable distance such as 2.0 to 8.0 centimeters to allow an ionic current flow between the positive and negative electrodes 71 and 72.

Upon energizing the direct current power supply 80, an ion current flows between the positive and negative electrodes 71 and 72. The direct ion current flow between the positive and negative electrodes 71 and 72 produces electrolytically free silver ions within the diluted organic acid solution 62. The silver ions react with the organic acid in the diluted organic acid solution 62 to produce the disinfectant 14 of the present invention.

The disinfectant 14 is directed by a conduit 86 to a settling tank 90. The settling tank 90 includes an overflow conduit 91 and a drain conduit 92. The disinfectant 14 exits the settling tank 90 through the overflow conduit 91. Any precipitated materials from the disinfectant 14 within the settling tank 90 fall to the bottom of the settling tank 90. The precipitated materials at the bottom of the settling tank 90 may be removed through the drain conduit 92 to a purge tank 100. The precipitated materials in the purge tank 100 may be recycled.

The disinfectant 14 exiting through the overflow conduit 91 from the settling tank 90 is directed to a particle filter 110. Although the particle filter 110 may be any suitable filter, preferably the particle filter 110 is a submicron filter. The filtered disinfectant 14 is directed to a valve 120 by a conduit 121. The valve 120 directs the filtered disinfectant 14 to a conduit 122 for discharge from the first process 10.

The filtered disinfectant 14 discharged from conduit 122 may be used immediately for any suitable application such as a disinfectant in a water system or any other suitable application. In the event a greater concentration of the disinfectant 14 is desired, the disinfectant 14 may be recirculated for increasing the concentration of the disinfectant 14.

Figure 2:
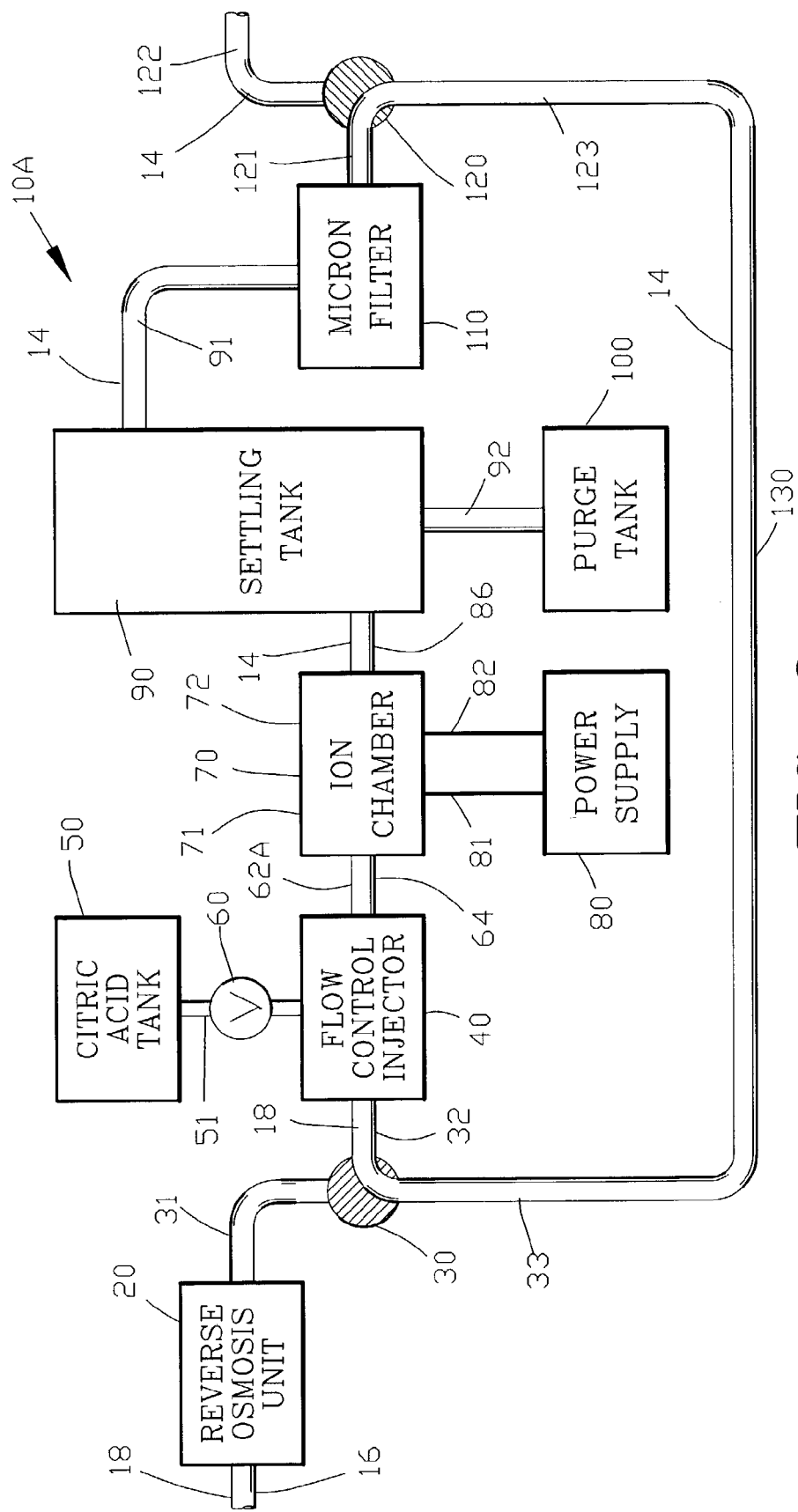
FIG. 2 is a diagram of a second process of making the disinfectant of the present invention.

FIG. 2 is a diagram of a second process 10A of making the disinfectant 14 of the present in a concentrated form. The second process 10A is shown as a recirculating process of making the disinfectant 14 and for increasing the concentration of the disinfectant 14. In the concentrated form, the disinfectant 14 may be bottled for use at a later time. It should be understood that the second process 10A of FIG. 2 is only an example of a process and numerous other variations and/or processes may be utilized to make the disinfectant 14 of the present invention.

In the second process 10A shown in FIG. 2, the valve 30 and 120 are moved into positions opposite to the positions shown in FIG. 1. The valve 120 directs the filtered disinfectant 14 to a conduit 123. The conduit 123 is connected through a conduit 130 to the conduit 32 of the valve 30.

The valve 30 directs the filtered disinfectant 14 though the conduit 32 to the flow control injector 40. Additional concentrated organic acid is directed through the metering valve 60 into the flow control injector 40. The flow control injector 40 mixes the concentrated organic acid with the filtered disinfectant 14 to increase the concentration of the organic acid solution 62A.

The organic acid solution 62A is directed into an ion chamber 70 to produce additional silver ions within the organic acid solution 62A. The silver ions react with the organic acid in the organic acid solution 62A to increase the concentration of the disinfectant 14. The disinfectant 14 is passed through the settling tank 90 to exit through the overflow conduit 91. The disinfectant 14 is filtered by the particle filter 110 and is directed to the valve 120 by the conduit 121.

The valve 30 and 120 are maintained in positions shown in FIG. 2 to continue to recirculate the disinfectant 14 for increasing the concentration of the disinfectant 14. Upon obtaining the desired concentration of the disinfectant 14, the valve 120 may be moved to the position shown in FIG. 1 to discharge the disinfectant 14 from the conduit 122.

Figure 4:
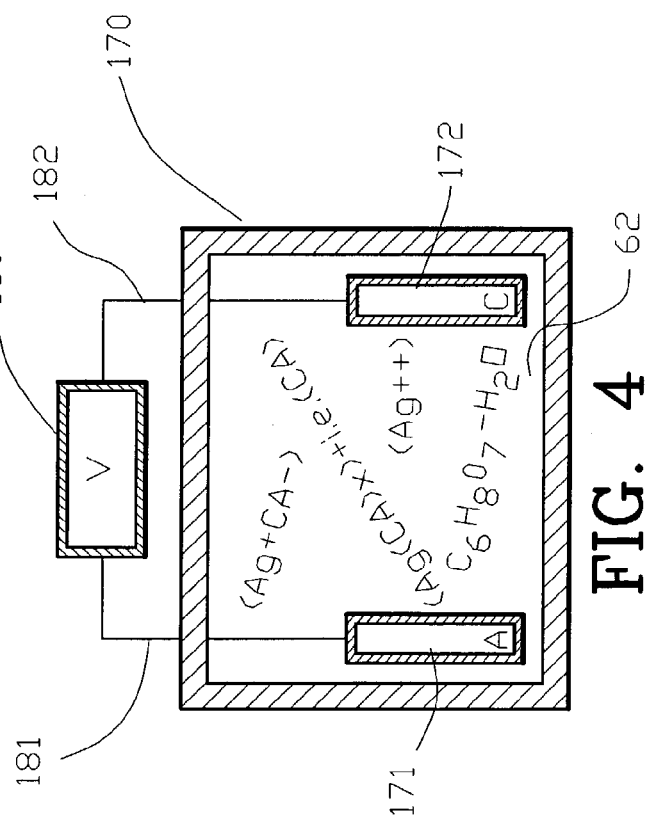
FIG. 4 is an enlarged detailed view of an ion chamber suitable for making the disinfectant of the present invention in a batch process.

FIG. 4 is an enlarged detailed view of an ion chamber 170 suitable for making the disinfectant of the present invention in a batch process. The ion chamber 170 includes a positive and a negative electrode 171 and 172. Each of the positive and negative electrodes 171 and 172 is fabricated from 99.9999% pure elemental silver.

The positive and negative electrodes 171 and 172 are located in a spaced apart position for enabling the organic acid solution 162 to pass between the positive and negative electrodes 171 and 172. Preferably, the positive silver electrode 171 is spaced relative to a negative electrode 172 a distance sufficient to enable silver ion flow therebetween. The spacing of the positive and negative electrodes 171 and 172 has been shown in an exaggerated fashion in FIG. 4. Preferably, a spacing of approximately 2.0 to 8.0 mm. has been found to be suitable for the above concentration of organic acid and water.

A direct current power supply 180 includes a positive and a negative conductor 181 and 182 connected to the positive and negative electrodes 171 and 172. Upon energizing the direct current power supply 180, an ion current flows between the positive and negative electrodes 171 and 172. The direct ion current flow between the positive and negative electrodes 171 and 172 produces electrolytically free silver ions within the organic acid solution 162. The silver ions react with the organic acid in the organic acid solution 162 to produce the disinfectant 14 of the present invention.

The process of making a disinfectant comprises electrolytically generating silver ions in a solution of organic acid and water to form an aqueous solution of silver ion organic acid complex. Preferably, the solution of organic acid and water comprises a solution of approximately 5.0% to 10% organic acid in water by volume. A potential difference of 12 volts to 50 volts provides a flow of silver ions in the range of 0.1 amperes to 0.5 amperes per square inch. A more fuller explanation of the content of the solution within the ion chamber 170 will be described in greater detail hereinafter.

The prior art has established in that the generation of both silver ions and copper ion in water provides the best disinfectant properties. The combination of silver ions and copper ions provides superior disinfecting properties than either silver ions alone or copper ions alone. This synergistic effect of silver ions and copper ions in water has been well established by the prior art.

In contrast to this established prior art, the disinfectant of the present invention is formed in a solution of organic acid and water rather than water alone. Additionally, the disinfectant of the present invention has superior properties with only silver ions alone rather than the combination of both silver ions and copper ions. The silver ions of the present process react with the organic acid to form the silver ion organic acid complex. The silver ion organic acid complex provides superior disinfectant properties over the prior art process of generating silver and copper ions in water.

In further contrast to the established prior art, the disinfectant of the present invention has a stable ionic form having an extended useful shelf-life. The useable shelf-life of the disinfectant of the present invention enables the aqueous disinfectant solution to be packaged in an aqueous concentrate form.

Specific Composition

In my prior U.S. patent application Ser. No. 09/169,229 filed Oct. 9, 1998, now U.S. Pat. No. 6,197,814, and Internation application PCT\US98\21604, I disclosed an aqueous disinfectant solution of silver organic acid complex wherein the silver is electrolytically generated in a solution of organic citric acid and water. An aqueous disinfectant solution of silver citrate has been tested and found to be a stable ionic form having an extended useful shelf-life. The extended useful shelf-life of the disinfectant enabled the disinfectant to be packaged in an aqueous concentrate form.

Concentrations of 0.7% by volume have been formulated in accordance with the above process. A concentration of 0.7% silver citrate by volume corresponds to 7000 parts per million (ppm). The concentration of 0.7% silver citrate was formed in a solution of organic acid and water comprises approximately 20-30% organic acid by volume. Higher concentration of the silver citrate in the range of 2.0% or greater by volume are believed to be obtainable by the above process. It appears the higher the concentration of organic acid in water, the higher the concentration of silver citrate formed by the above process. The above weight/volume may be a weight/weight depending on whether the components are solid/liquid or solid/solid.

The silver citrate was found to be stable in a concentration of 5.0% and 10% citric acid solutions. The stability of the silver citrate in the 1.0% citric acid solution experienced significant reductions in stability. The minimum concentration of the citric acid solution is therefore some value greater than 1.0%. The maximum concentration of the citric acid in the aqueous solution has not been determined by test. However, it is believed that the maximum concentration of the citric acid in the aqueous solution will be much greater than 10.0%. It is also evident from these results, that the higher the concentration of the citric acid in the aqueous solution, the greater the concentration of silver ions that can be stabilized.

Nuclear magnetic resonance tests (1H NMR) were preformed on the silver citrate formed in accordance with the above process and a blank organic acid sample. The samples showed an overwhelming excess of organic acid, with little or no other anions present. It is postulated the Ag must be in the form of the cation Ag+ complexed with the organic acid. It is theorized the empty 5 s orbital of Ag+ overlaps with the delocalized π bond on one of the carboxyl groups of organic acid. The organic acid anion is the counterion for this complex ion (Ag(OA)x)+ i.e. (OA)−. Another possibility is a zwitterion, where the negative charge is on the complex itself, (Ag+CA−) where the total charge of the complex is neutral. Either or both of these species may exist in the silver ion organic acid complex formed in accordance with the above process. Multiple complexation to Ag+ is also possible.

The complete results of silver organic acid complex with the organic acid being citric acid is set forth in my prior U.S. patent application Ser. No. 09/169,229 filed Oct. 9, 1998, now U.S. Pat. No. 6,197,814, and International application PCT\US98\21604, which is hereby incorporated by reference into the present application as if fully set forth herein.

Other Organic Acids

The present invention expands upon the acids suitable for use for forming the silver ion organic acid complex of the present invention. The silver is electrolytically generated in a solution of the organic acid and water. In a first example of the invention, the organic acid selected from a group I consisting of ascorbic acid, citric acid, glycollic acid, lactic acid, malic acid and/or tartaric acid.

In a second example of the invention, the organic acid selected from a group II consisting of acetic acid, aspartic acid, cis-cyclohexane dicarboxylic acid, chloracetic acid, malic, malonic acid, propionic acid and/or succinic acid and the amino acids dl-cysteine and cystine.

In a third example of the invention, the organic acid selected from a group III consisting of amino acids, dl-cysteine and dl-cystine.

The group I consisting of ascorbic acid, citric acid, glycollic acid, lactic acid, maleic acid, tartaric acid are organic acids having the characteristic of an acid as well as the characteristic of an alcohol. The group II consisting of acetic acid, aspartic acid, cis-cyclohexane dicarboxylic acid, chloracetic acid, malic, malonic acid, propionic acid and/or succinic acid and the amino acids dl-cysteine and cystine are organic acids having the characteristic of an acid. The group III consisting of amino acids, dl-cysteine and dl-cystine have different characteristics than Group I and Group II.

Enhanced Formulations

An enhanced formulation of the improved disinfectant of the present invention includes the addition of an alcohol. In one example of the second formulation of the improved disinfectant, ethyl alcohol (ETOH) is added in an approximate amount of 20% by volume. However, it should be understood that other types of alcohols may be added to the second formulation of the improved disinfectant of the present invention.

Another enhanced formulation of the improved disinfectant of the present invention includes the addition of a detergent. In one example of the third formulation of the improved disinfectant, sodium dodecyl sulfate is added in an approximate amount of up to 2% by volume.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A process of making a silver ion-organic acid complex, comprising the step of:
electrolytically generating silver in a solution of greater than 1% organic acid and water to form an aqueous solution of a silver ion-organic acid complex, wherein the organic acid has the characteristic of an acid as well as the characteristic of an alcohol.

2. A process of making a silver ion-organic acid complex, comprising the step of:
electrolyically generating silver in a solution of greater than 1% organic acid and water to form an aqueous solution of a silver ion-organic acid complex, wherein the organic acid is selected from the group consisting of ascorbic acid, citric acid, glycolic acid, lactic acid, malic acid and tartaric acid.

3. A process of making a silver ion-organic acid complex, comprising the step of electrolytically generating silver in a solution of greater than 1% organic acid and water to form an aqueous solution of silver ion-organic acid complex, wherein the step of electrolytically generating silver includes forming a complex with the organic acid, said organic acid being selected from the group consisting of acetic acid, aspartic acid, cis-cyclohexane dicarboxylic acid, chloroacetic acid, dl-cysteine, dl-cystine malic acid, malonic acid, propionic acid, and succinic acid.

4. The process of claim 3, wherein said organic acid is acetic acid.

5. The process of claim 3, wherein said organic acid is aspartic acid.

6. The process of claim 3, wherein said organic acid is cis-cyclohexane dicarboxylic acid.

7. The process of claim 3, wherein said organic acid is chioroacetic acid.

8. The process of claim 3, wherein said organic acid is malic acid.

9. The process of claim 3, wherein said organic acid is malonic acid.

10. The process of claim 3, wherein said organic acid is propionic acid.

11. The process of claim 3, wherein said organic acid is succinic acid.

12. The process of claim 3, wherein said organic acid is dl-cysteine.

13. The process of claim 3, wherein said organic acid is cystine.

* * * * *